United States Patent
Kiene

[11] Patent Number: 5,673,905
[45] Date of Patent: Oct. 7, 1997

[54] CLAMP DEVICE FOR CLAMPING SPECIMEN HOLDERS FOR A MICROTOME

[75] Inventor: Uwe Kiene, Nusslock, Germany

[73] Assignee: Leica Instruments GmbH, Wetzlar, Germany

[21] Appl. No.: 535,912

[22] Filed: Sep. 28, 1995

[30] Foreign Application Priority Data

Sep. 28, 1994 [DE] Germany ............... 9415681 U

[51] Int. Cl.$^6$ .................................................... B25B 1/04
[52] U.S. Cl. ................ 269/238; 269/240; 269/244; 269/289 R; 269/303; 269/329
[58] Field of Search ............... 269/240, 244, 269/238, 265, 269, 270, 259, 289 R, 303, 305, 329, 290, 291, 258, 909, 58, 59, 76, 81, 82, 83

[56] References Cited

U.S. PATENT DOCUMENTS

| 577,845 | 5/1897 | Eckert | 269/246 |
|---|---|---|---|
| 1,690,611 | 11/1928 | Zimmermann | 269/244 |
| 2,422,773 | 6/1947 | Colwill | 269/238 |
| 2,429,801 | 10/1947 | Butler | 269/240 |
| 3,550,245 | 12/1970 | Davis | 269/290 |
| 4,278,263 | 7/1981 | Rosen | 279/1 |
| 4,383,682 | 5/1983 | Feinberg | 269/258 |
| 4,410,169 | 10/1983 | Swenson | 269/32 |
| 4,953,839 | 9/1990 | Chern | 269/73 |
| 5,417,409 | 5/1995 | Reddell | 269/25 |
| 5,499,802 | 3/1996 | Haberle | 269/305 |

FOREIGN PATENT DOCUMENTS

| 30 40 217 | 5/1981 | Germany . |
| 33 27 618 | 2/1985 | Germany . |
| 1190944 | 5/1970 | United Kingdom . |

Primary Examiner—Timothy V. Eley
Assistant Examiner—Lee Wilson
Attorney, Agent, or Firm—Foley & Lardner

[57] ABSTRACT

A clamp device for clamping a specimen holder. The clamp device includes a rotatably mounted clamping lever, a rotatable clamping wedge, and a guide member which is located adjacent to the clamping wedge for receiving the specimen holder. The clamping wedge is in operative communication with the clamping lever, so that by rotating the clamping lever, the clamping wedge is rotated into the guide member which causes the specimen holder to be clamped within the guide member. The specimen holder may be provided with a removable adapter plate wherein the adapter plate is sized to fit within the guide member. By including the adapter plate, multiple sizes and types of specimen holders can thereby be employed using the same clamping device.

6 Claims, 3 Drawing Sheets

CLAMP DEVICE FOR CLAMPING SPECIMEN HOLDERS FOR A MICROTOME

BACKGROUND OF THE INVENTION

1. Field of the Invention

The present invention relates to a clamp device for clamping specimen holders for a microtome.

2. Description of the Related Art

Clamp devices are used in microtomes, particularly in rotary microtomes, for the purpose of securing different-sized specimen holders on the microtome via a single receiver. To this end, however, it is necessary that the widely varying specimen holders be oriented with precision in relation to the setting of the cutting blade.

DE 33 27 618 C2 discloses a device for clamping a specimen piece in a microtome, in which the clamp device is mounted in a displaceable manner on a carriage. The round specimen holder is connected to the clamp device via a ring nut. This type of securing satisfies the required precision as regards the orientation of the specimen holder relative to the cutting blade. However, changing the specimen holder via the ring nut is possible only with some difficulty. In addition, as a result of the small spacing from the cutting blade, there is always the risk of cutting and injuring oneself when changing specimen holders. That is, because the ring nut is located only a short distance from the blade, it is easy to inadvertently cut oneself. A further disadvantage of this clamp device is that only specimens of a quite specific size and shape can be accommodated. It is found in practice that, in addition to the round specimens, other specimen shapes embedded in paraffin are often prepared. Accordingly, each different specimen shape requires a special holder which may or may not be capable of being used in conventional clamp devices.

SUMMARY OF THE INVENTION

It is therefore an object of the present innovation to provide a clamp device which accommodates a great variety of specimen holders. It is a further object to provide a clamp device which additionally permits straightforward and precise changing of the specimens.

According to the present invention, these objects are achieved by providing a clamp device for clamping a specimen holder which includes a rotatably mounted clamping lever, a rotatable clamping wedge, and a guide member which is located adjacent to the clamping wedge for receiving the specimen holder. The clamping wedge is in operative communication with the clamping lever, so that by rotating the clamping lever, the clamping wedge is rotated into the guide member which causes the specimen holder to be clamped within the guide member. The specimen holder may be provided with a removable adapter plate wherein the adapter plate is sized to fit within the guide member. By including the adapter plate, multiple sizes and types of specimen holders can thereby be employed using the same clamping device.

In contrast to the formerly very laborious effort required for any changing of the various specimen holders by screw fasteners, with the present invention it is now possible to make a quick change of the individual specimen holders on the microtome.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out in the appended claims.

BRIEF DESCRIPTION OF THE DRAWINGS

The accompanying drawings, which are incorporated in and constitute a part of the specification, illustrate a presently preferred embodiment of the invention, and, together with the general description given above and the detailed description of the preferred embodiment given below, serve to explain the principles of the invention.

DETAILED DESCRIPTION OF THE PREFERRED EMBODIMENTS

Figure 1:
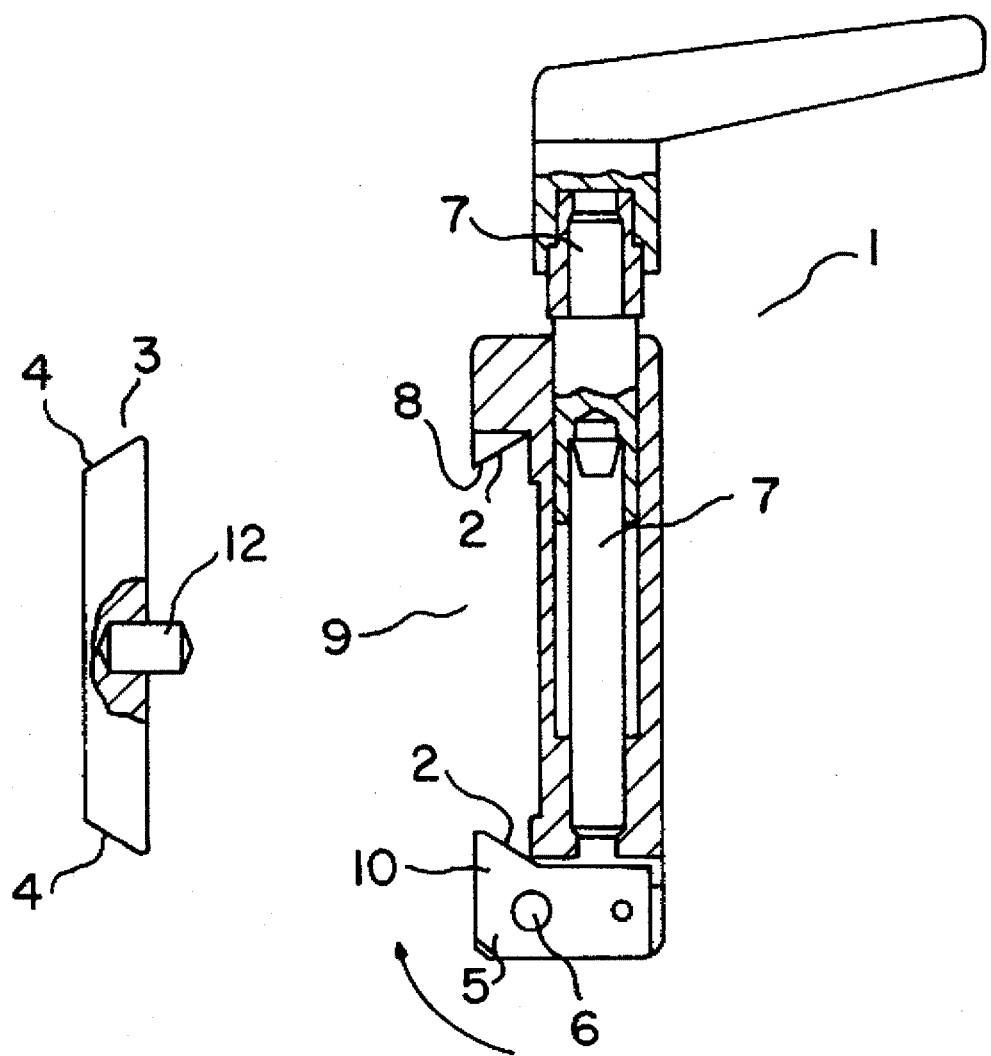
FIG. 1 shows a side view in partial cross section of the clamp device and the adapter plate according to the present invention.

FIG. 1 shows a section through the clamp device 1 of the present invention which is secured on a holding arm of a rotation microtome (not shown). The clamp device 1 has a guide 9 which is preferably dovetail in shape, with guide surfaces 2 and support surfaces 8 for receiving a portion of a specimen holder. In a preferred embodiment, the specimen holder includes an adapter plate 3 which is received by the guide 9. The specimen holder or adapter plate 3 is provided with corresponding guide surfaces 4 which are sized to allow the same to be positioned within the guide 9.

The guide surfaces 2 on the clamp device i and the guide surfaces 4 of the adapter plate 3 are wedge-shaped. See FIGS. 1 and 4. These surfaces are interrupted by the clamping wedge 5, described below.

For the purpose of clamping the specimen holder and/or adapter plate 3 in the clamp device 1, a clamping wedge 5 is provided on the clamp device 1. The clamping wedge 5 is mounted so as to rotate about an axis 6 and is in operative communication with a rotatably mounted clamping lever 7 for locking the specimen holder, so that by turning the lever 7, the clamping wedge 5 is swiveled with its wedge-shaped section 10 against the guide surfaces 4 of the adapter plate 3. The center of gravity of the clamping wedge 5 lies outside its axis of rotation 6, so that when the adapter plate 3 is pushed into the clamp device 1, the wedge-shaped section 10 of the clamping wedge 5, which section 10 is provided for the clamping, stands back from the guide surfaces 2. Only by turning the clamping lever 7 is the clamping wedge 5 moved in the direction of the arrow toward the guide surfaces 4 of the adapter plate 3, so that the clamping between the adapter plate 3 and the clamp device i is effected via the support surfaces 8 of the guide 9. That is, the wedge-shaped section 10 of the clamping wedge 5 is not disposed within the guide 9 until the lever 7 is rotated. This arrangement permits the adapter plate 3 to be easily placed within the guide 9 without being impeded by any portion of the clamping wedge 5.

The adapter plate 3 with its guide surfaces 4 corresponding to the guide 9 of the clamp device 1 is connected to a given specimen holder (not illustrated). As stated supra, the adapter plate is preferred, however, it is contemplated that the specimen holder itself may be adapted to fit within the guide 9 of the clamp device 1. The adapter plate 3 additionally is provided with a limit stop pin 12. This pin 12 is assigned a corresponding limit stop groove 13 (See FIG. 2) provided within the clamp device 1.

Figure 2:
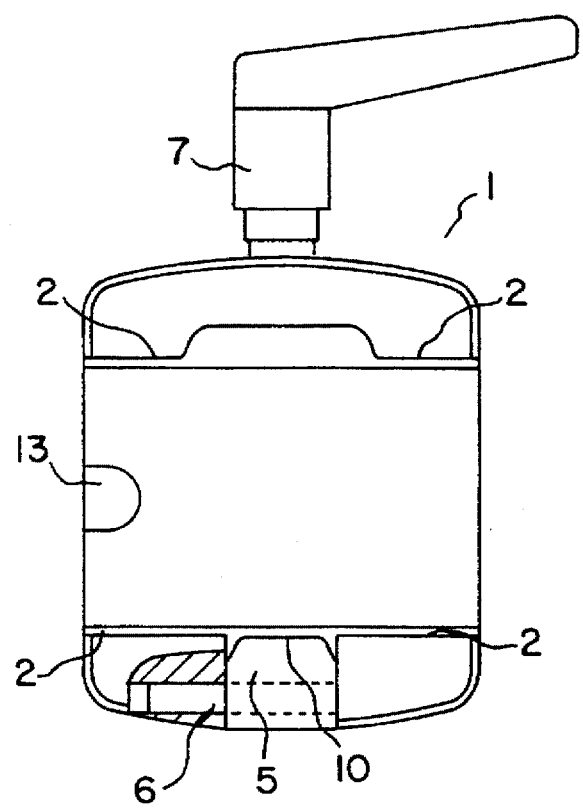
FIG. 2 shows a front view of the clamp device.

FIG. 2 shows a front view of the clamp device 1 which details the limit stop groove 13 and the guide surfaces 2 of the guide 9. The limit stop groove 13 guarantees, together with the limit stop pin 12 arranged on the specimen holder or adapter plate 3, a precise positional fixing of the specimen holder in the clamp device, so that subsequent alignment of the specimen in relation to the cutting blade of the microtome can be dispensed with. The clamping wedge 5 with its axis of rotation 6 and its wedge-shaped section 10 is positioned out of the way from the guide surface 2, so that an unimpeded insertion of the adapter plate 3 with the specimen holder arranged thereon is guaranteed.

Figure 4:
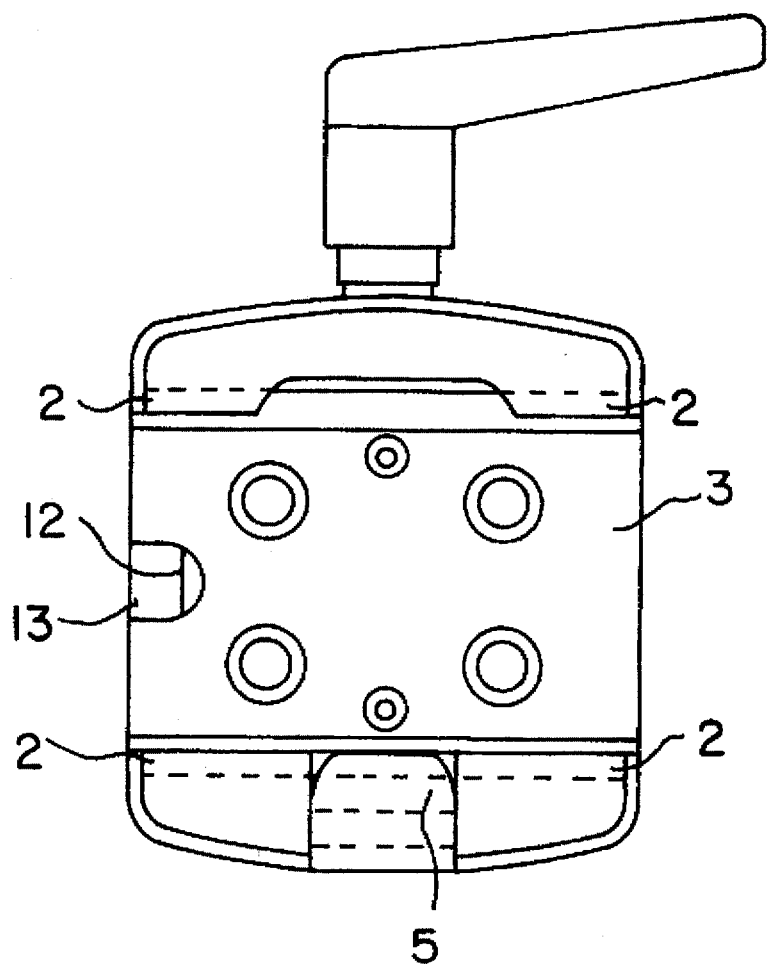
FIG. 4 shows the adapter plate inserted into the clamp device.

The adapter plate 3 with the limit stop pin 12 is laterally inserted into the clamp device and securely guided by the dovetail guide 9. The dovetail guide 9 prevents any twisting or tipping of the adapter plate 3. The positioning of the adapter plate 3 in the clamp device is accomplished by the dovetail guide 9 and the limit stop pin 12 provided on the adapter plate 3, since a corresponding limit stop groove 13 is provided in the adapter plate. The pin 12 engages the groove 13 and thus prevents the adapter plate from being pushed further in the clamp device, as shown in FIG. 4.

Figure 3:
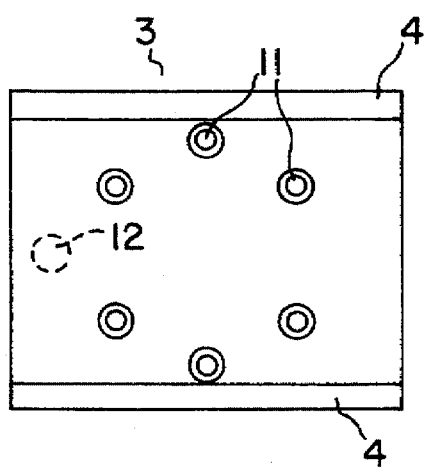
FIG. 3 shows a front view of the adapter plate.

FIG. 3 shows a front view of the adapter plate 3 with the guide surfaces 4. The adapter plate 3 is also provided with bores 11 for securing a specimen holder (not illustrated) of any desired size. In one preferred embodiment, the adapter plate 3 is designed as a component which can be retrofitted, and it is connected in a releasable manner to the specimen holder.

The illustrative embodiment of the clamp device which has been described and which is illustrated in the drawings is distinguished not only by its simple construction, but also by its ergonomically convenient handling, since the specimen holder with the adapter plate can be changed safely and with precision by simple insertion into the clamp device.

The present invention is not limited to the illustrative embodiment which has been described and illustrated. It is entirely within the scope of the innovation to connect the adapter plate in a fixed manner to the specimen holder and/or to equip the specimen holder directly with a guide of this type.

Additional advantages and modifications will readily occur to those skilled in the art. Therefore, the invention in its broader aspects is not limited to the specific details, and representative devices, shown and described herein. Accordingly, various modifications may be made without departing from the spirit or scope of the general inventive concept as defined by the appended claims and their equivalents.

What is claimed is:

1. A clamp device for clamping a specimen holder for a microtome comprising:
   a specimen holder adapter plate having guide surfaces;
   a rotatably mounted clamping lever;
   a guide member which receives said adapter plate, said guide member having guide surfaces which correspond to the guide surfaces of said adapter plate; and;
   a rotatable clamping wedge having an axis of rotation, said clamping wedge being provided adjacent to one of said guide surfaces of said guide member, said clamping wedge being operatively associated with said rotatable clamping lever, wherein the center of gravity of the clamping wedge lies outside said axis of rotation of said clamping wedge so that the clamping wedge is not disposed within said guide member until said lever is rotated, thus permitting said adapter plate to be placed within said guide member without being impeded by said clamping wedge;
   wherein when said adapter plate is inserted within said guide member, by turning said clamping lever, said clamping wedge is rotated against at least one of the guide surfaces of said adapter plate to clamp the adapter plate within said guide member.

2. A clamp device as claimed in claim 1, wherein the adapter plate is releasably connected to a specimen holder.

3. A clamp device for clamping a specimen holder for a microtome comprising:
   a specimen holder adapter plate having guide surfaces;
   a rotatably mounted clamping lever;
   a guide member which receives said adapter plate, said guide member having guide surfaces which correspond to the guide surfaces of said adapter plate; and;
   a rotatable clamping wedge having an axis of rotation, said clamping wedge being provided adjacent to one of said guide surfaces of said guide member, said clamping wedge being operatively associated with said rotatable clamping lever;
   wherein when said adapter plate is inserted within said guide member, by turning said clamping lever, said clamping wedge is rotated against at least one of the guide surfaces of said adapter plate to clamp the adapter plate within said guide member, wherein the adapter plate is provided with a limit stop pin and said clamp device is provided with a corresponding limit stop groove which receivingly accepts said limit stop pin therein, said pin being capable of engaging said groove so as to prevent said adapter plate from being further inserted within said guide member.

4. A clamp device as claimed in claim 1, wherein said guide member is dovetail shaped.

5. A clamp device for clamping a specimen holder comprising:
   a rotatably mounted clamping lever;
   a guide member for receiving said specimen holder;
   a rotatable clamping wedge having an axis of rotation for holding said specimen holder within said guide, said clamping wedge having a center of gravity, and said clamping wedge being in operative communication with said clamping lever, such that by rotating said clamping lever, said clamping wedge is rotated into said guide member so as to retain said specimen holder therewithin, wherein the center of gravity of the clamping wedge lies outside its axis of rotation so that the clamping wedge is not disposed within said guide member until said lever is rotated, thus permitting an adapter plate to be placed within said guide member without being impeded by said clamping wedge.

6. A clamp device as claimed in claim 5, wherein said guide member is dovetail in shape.

* * * * *